(12) United States Patent
Akagi

(10) Patent No.: US 9,579,176 B2
(45) Date of Patent: Feb. 28, 2017

(54) BRUSH FOR CLEANING INSIDE OF IMPLANT

(75) Inventor: Homare Akagi, Osaka (JP)

(73) Assignee: Homareproducts Corporation, Osaka (JP)

( * ) Notice: Subject to any disclaimer, the term of this patent is extended or adjusted under 35 U.S.C. 154(b) by 618 days.

(21) Appl. No.: 13/884,690

(22) PCT Filed: Nov. 10, 2011

(86) PCT No.: PCT/JP2011/006304
§ 371 (c)(1),
(2), (4) Date: Aug. 23, 2013

(87) PCT Pub. No.: WO2012/063496
PCT Pub. Date: May 18, 2012

(65) Prior Publication Data
US 2013/0327354 A1    Dec. 12, 2013

(30) Foreign Application Priority Data

Nov. 11, 2010 (JP) .................................. 2010-253319

(51) Int. Cl.
*A46B 3/18* (2006.01)
*A61C 17/22* (2006.01)
(Continued)

(52) U.S. Cl.
CPC ................ *A61C 17/26* (2013.01); *A46B 3/18* (2013.01); *A46B 13/02* (2013.01); *A46D 1/0207* (2013.01);
(Continued)

(58) Field of Classification Search
CPC ........... A46B 3/18; A61C 15/00; A61C 17/22; A61C 17/26; A61C 17/222
See application file for complete search history.

(56) References Cited

U.S. PATENT DOCUMENTS 5,699,578 A    12/1997 Dumler
6,179,617 B1    1/2001 Ruddle
(Continued)

FOREIGN PATENT DOCUMENTS

CH    667382 A5    10/1988
DE    40 19 830    *    1/1992
(Continued)

OTHER PUBLICATIONS

PCT International Search Report for PCT International Patent Application No. PCT/JP2011/006304, mailed Jan. 17, 2012.
(Continued)

*Primary Examiner* — Randall Chin
(74) *Attorney, Agent, or Firm* — Holland & Hart LLP

(57) ABSTRACT

Devices and methods for keeping an internal cavity of an implant or specifically an internal cavity provided in a fixture constituting an implant in a clean state by a simple operation without injuring the gingiva around the fixture is provided. A brush for cleaning the inside of an implant provided with a twisted brush part in which helical brush bristles are formed around the wire rod by arranging a large number of resin fibers in parallel in a direction perpendicular to a wire rod and then, by twisting the wire rod, an intermediate columnar part to which the twisted brush part is fixed, and a main columnar part to which the intermediate columnar part is fixed, where a length in a major axis direction of the intermediate columnar part is within a range of 0.8 to 2.0, assuming that a length in a major axis direction of the twisted brush part is 1.

7 Claims, 7 Drawing Sheets

(51) Int. Cl.

| | | |
|---|---|---|
| *A61C 17/26* | (2006.01) | |
| *A61C 3/00* | (2006.01) | |
| *A61C 8/00* | (2006.01) | |
| *A46B 13/02* | (2006.01) | |
| *A46D 1/00* | (2006.01) | |
| *A46B 3/08* | (2006.01) | |
| *A46B 3/16* | (2006.01) | |

(52) U.S. Cl.
CPC ............... *A61C 3/005* (2013.01); *A61C 8/00* (2013.01); *A61C 17/222* (2013.01); *A46B 3/08* (2013.01); *A46B 3/16* (2013.01); *A61C 8/0089* (2013.01)

(56) References Cited

U.S. PATENT DOCUMENTS

| | | | |
|---|---|---|---|
| 7,721,379 B2 | 5/2010 | Takahashi | |
| 2010/0163073 A1* | 7/2010 | Lyngstadaas | A46B 3/18 134/8 |

FOREIGN PATENT DOCUMENTS

| | | |
|---|---|---|
| JP | H08266338 A | 10/1996 |
| JP | H1133042 A | 2/1999 |
| JP | 2002177304 A | 6/2002 |
| JP | 2004-41260 * | 2/2004 |
| JP | 3615752 B1 | 2/2005 |
| JP | 2009-247585 * | 10/2009 |
| WO | 2009031396 A1 | 3/2009 |
| WO | 2009083281 A1 | 7/2009 |

OTHER PUBLICATIONS

Opinion and Amendment to extended European Search Report for European Patent Application No. 11839715.7, mailed Dec. 15, 2014 (pp. 23).

Communication pursuant to Article 94(3) EPC in European Patent Application No. 11839715.7, mailed Mar. 17, 2015 (pp. 4).

Supplementary European Search Report for International Application No. EP11839715, mailed Jun. 10, 2014 (2 pages).

* cited by examiner

BRUSH FOR CLEANING INSIDE OF IMPLANT

TECHNICAL FIELD

The present invention relates to a brush for cleaning the inside of an implant and more particularly to a brush for cleaning an internal cavity of a fixture constituting an implant used as an artificial dental root.

BACKGROUND ART

Some of patients having problems relating to teeth have their teeth which should have been present lost due to the reasons such as removal by an operation for decayed tooth, periodontal disease or the like, natural loss and the like.

If all the teeth are present, an individual tooth is usually supported by adjacent teeth and can fully exert its function.

However, if even one of the teeth which should have been present is missing, supporting bodies of the teeth located on both ends of the missing portion decrease and thus, a force for chewing things in mastication cannot be fully exerted. Moreover, if an individual interdental space is expanded by loss of a tooth, food residues and the like can easily remain in the interdental space and thus, further occurrence of periodontal diseases or decayed teeth progresses.

As a measure against such problems occurring due to missing of a tooth, an operation of an implant on a portion where a missing tooth used to be is widely employed.

An implant is a type of an artificial dental root and is usually formed of a fixture to be embedded in a bone and an abutment which is connected to the fixture and serves as a supporting base. By attaching an artificial tooth on the abutment, the artificial tooth can be installed on a portion where a tooth is missing.

FIG. 8 illustrates a schematic perspective view of a fixture used in a prior-art implant for reference.

A usual method of operation for installing an implant will be described below.

First, gingiva covering a portion where a missing tooth used to be present is separated, a drill hole is drilled in the bone and then, a fixture 300 illustrated in FIG. 8 is embedded in the drill hole.

At a stage when the fixture 300 is installed in the bone, the gingiva of the patient is injured and swollen and thus, return to a healthy state of the gingiva is waited for and then, the abutment and the artificial tooth are mounted on the fixture 300.

An internal cavity 310 is provided in the fixture 300, and by screwing the abutment in this internal cavity 310, the abutment can be fixed to the fixture 300.

However, a certain period is required until the state of the gingiva of the patient becomes stable after the fixture 300 is installed in the bone. Thus, it is likely that a bone fragment, a gingival fragment, blood or the like remains in the internal cavity 310 of the fixture 300 or food residues generated during daily meals and the like collect in the internal cavity 310 of the fixture 300.

In order to eliminate the possibility that the bone fragment, gingival fragment, blood or the like and food residues collect in the internal cavity 310 of the fixture 300, such a measure can be proposed that a professional operator such as a dentist performs cleaning so as to keep the internal cavity 310 in a clean state.

However, a diameter of the internal cavity 310 of the fixture 300 used in an implant is usually very small at approximately 3 mm or less, and there is limitation in keeping the internal cavity 310 in a clean state during an operation of an implant, attachment of a healing cap and an abutment and the like.

On the other hand, there can be a method of embedding the fixture 300 of a type having a lid from the beginning on the internal cavity 310 in the bone.

However, if a lid is provided on the internal cavity 310 having a diameter of approximately 3 mm or less, a work of taking off the lid becomes extremely complicated and the operation takes time and in addition, there is a concern that the gingiva around the fixture 300 of the patient is injured during the work of removing the lid.

Moreover, if a prior-art brush used for polishing of teeth is attached to a high-speed rotating device called a micromotor having been used for polishing of teeth in order to clean the internal cavity 310 of the fixture 300, it is extremely difficult to insert the prior-art brush into only the internal cavity 310 of the fixture 300, and it is also likely that the gingiva in the vicinity of the fixture 300 of the patient is injured.

On the other hand, a small-diameter resin twisted brush with the purpose of interdental cleaning has been proposed.

However, this small-diameter resin twisted brush is a twisted brush in which helical brush bristles are formed around a shaft member and can be used in the perpendicular direction to the surface of a tooth, but it is difficult to use it in the vertical direction to the bone serving as a base of a tooth, that is, in the vertical direction along the surface of the tooth (Patent Literature 1).

The interdental brush represented by the small-diameter resin twisted brush should be used in the perpendicular direction to the surface of a tooth and its working mechanism is totally different from a brush for cleaning the inside of an implant used in the horizontal direction to the surface of a tooth and cannot be referred to in development of a brush for cleaning the inside of an implant.

CITATION LIST

Patent Literature

Patent Literature 1: Japanese Patent No. 3615752

SUMMARY OF INVENTION

Technical Problem

The present invention has an object to provide means for keeping an internal cavity of an implant or more specifically, an internal cavity provided in a fixture constituting an implant in a clean state by a simple operation without injuring the gingiva around the fixture.

Solution to Problem

In order to solve the above-described problems, the inventor has made a keen examination and as a result, found out that a brush for cleaning the inside of an implant provided with a twisted brush part in which a helical brush bristles are formed around a wire rod, an intermediate columnar part to which the twisted brush part is fixed, and a main columnar part to which the intermediate columnar part is fixed meets the object of the present invention and has completed the present invention.

That is, the present invention is to provide

[1] a brush for cleaning the inside of an implant provided with:

a twisted brush part formed by arranging a large number of resin fibers in parallel in a direction perpendicular to a wire rod and then, by twisting said wire rod so as to provide helical brush bristles around said wire rod;

an intermediate columnar part; and a main columnar part, in which the wire rod used in the twisted brush part is fixed to one of end portions of the intermediate columnar part so that the twisted brush part and the intermediate columnar part are fixed to each other;

the main columnar part is fixed to the other end portion of the intermediate columnar part is fixed;

the main columnar part has a rotating device mounting part on the other end portion opposite to the one end portion to which the intermediate columnar part;

a major axis center line of the intermediate columnar part matches a major axis center line of the main columnar part; and on the basis of the major axis center line direction of the intermediate columnar part, assuming that the length of the twisted brush part is 1, the length of the intermediate columnar part is in a range of 0.8 to 2.0.

Moreover, one of the present invention is to provide the brush for cleaning the inside of an implant described in the above-described [1], in which

[2] a projection plane of the intermediate columnar part from the major axis center line direction to a plane perpendicular to the major axis center line of the intermediate columnar part is contained within a projection plane of the twisted brush part from the major axis center line direction to the plane perpendicular to the major axis center line of the intermediate columnar part; and the projection plane of the intermediate columnar part from the major axis center line to the plane perpendicular to the major axis center line direction of the intermediate columnar part is contained within the projection plane of the main columnar part from the major axis center line direction to the plane perpendicular to the major axis center line direction of the main columnar part.

Moreover, one of the present invention is to provide the brush for cleaning the inside of an implant described in any one of the above-described [1] or [2], in which

[3] the twisted brush part is formed by arranging a large number of resin fibers in parallel with two wire rod parallel parts obtained by smoothly bending and folding back one wire rod and then, by twisting the two wire rod parallel parts so as to form a distal end portion of the twisted brush part having a smooth curved shape and by forming helical brush bristles around the wire rod.

Moreover, one of the present invention is to provide the brush for cleaning the inside of an implant described in any one of the above-described [1] to [3], in which

[4] the rotating device mounting part of the main columnar part includes a notched part provided in a planar direction horizontal to the major axis direction of the main columnar part and a groove part provided in an outer periphery of the main columnar part.

Moreover, one of the present invention is to provide the brush for cleaning the inside of an implant described in any one of the above-described [1] to [4], in which

[5] the distal end portion of the twisted brush part is provided with brush bristles in the major axis center line direction of the intermediate columnar part.

Moreover, one of the present invention is to provide the brush for cleaning the inside of an implant described in any one of the above-described [1] to [5], in which

[6] at least one selected from a group consisting of the wire rod of the twisted brush part, the intermediate columnar part, and the main columnar part is covered by a resin.

Moreover, one of the present invention is to provide the brush for cleaning the inside of an implant described in any one of the above-described [1] to [6], in which

[7] the length in the major axis direction of the twisted brush part is 8 mm±3 mm, the length in the major axis direction of the intermediate columnar part is 9 mm±3 mm, and the length in the major axis direction of the main columnar part is 17 mm±5 mm; and a maximum diameter appearing on a section in the direction perpendicular to the major axis direction of the intermediate columnar part is 1 mm±0.3 mm, and a maximum diameter appearing on a section in the direction perpendicular to the major axis direction of the main columnar part is 2.1 mm±1 mm.

Moreover, the present invention is

[8] to provide a method of cleaning the inside of an implant, in which the brush for cleaning the inside of an implant described in any one of the above-described [1] to [7] is attached to a rotating device and while the brush for cleaning the inside of an implant is rotated, a twisted brush part in which helical brush bristles of the brush for cleaning the inside of an implant are formed is inserted into an internal cavity provided in a fixture constituting the implant characterized in that a rotation speed of the brush for cleaning the inside of an implant is within a range of 100 to 1000 rpm; and a rotating direction of the helical brush bristles of the brush for cleaning the inside of an implant is a direction for discharging contents in the internal cavity from the inside of the internal cavity to the outside.

Advantageous Effects of Invention

The brush for cleaning the inside of an implant according to the present invention has the twisted brush part in which helical brush bristles are formed. Thus, the brush for cleaning the inside of an implant has a structure in which, by inserting the helical brush bristles into the internal cavity provided inside the implant, that is, in the fixture constituting the implant and rotating the helical brush bristles in a certain direction, a bone fragment, gingival fragment, blood and the like of a patient or food residues and the like generated during usual daily meals and the like inside the internal cavity adhering to the helical brush bristles can be discharged to the main columnar part side of the brush for cleaning the inside of an implant. As a result, the inside of an implant can be cleaned.

Moreover, since in the brush for cleaning the inside of an implant according to the present invention, the major axis center line of the intermediate columnar part matches the major axis center line of the main columnar part, vibration in the brush for cleaning the inside of an implant generated when the brush for cleaning the inside of an implant is rotated can be prevented.

The projection plane of the internal columnar part from the major axis center line direction to the plane perpendicular to the major axis center line of the intermediate columnar part is contained within the projection plane of the twisted brush part from the major axis center line direction to the plane perpendicular to the major axis center line of the intermediate columnar part; and the projection plane of the intermediate columnar part from the major axis center line direction to the plane perpendicular to the major axis center line of the intermediate columnar part is contained within the projection plane of the major columnar part from the major axis center line direction to the plane perpendicular to the major axis center line direction of the main columnar part.

That is, the intermediate columnar part has an outer diameter equal to or smaller than the maximum outer diameter of the twisted brush part in which the helical brush bristles are formed and an outer diameter equal to or smaller than the maximum outer diameter of the main columnar part.

Thus, when the helical brush bristles are inserted into the internal cavity provided in the fixture constituting the implant, since visibility to the twisted brush part in which the helical brush bristles are formed is excellent, the helical brush bristles can be inserted into the internal cavity provided in the fixture constituting the implant appropriately and easily, which is excellent in handling.

In addition, since the rotating intermediate columnar part has a configuration which is not easily brought into contact with a gingival part in the vicinity of the fixture constituting the implant, an effect that the gingival part in the vicinity of the fixture is not injured during cleaning of the inside of an implant can be exerted.

Moreover, regarding the brush for cleaning the inside of an implant according to the present invention, the brush bristles can be installed on the distal end portion of the twisted brush part in the major axis center line direction of the intermediate columnar part. By using the brush bristles, the internal cavity provided in the fixture constituting the implant can be cleaned.

Moreover, in the brush for cleaning the inside of an implant according to the present invention, at least one selected from a group consisting of the wire rod of the twisted brush part, the intermediate columnar part, and the main columnar part can be covered by a resin. By means of covering, even if the fixture constituting the implant and the brush for cleaning the inside of an implant are formed of different metal materials, ionization of the metal materials can be prevented, and generation of impurities can be prevented. Moreover, corrosion of the fixture constituting the implant and the brush for cleaning the inside of an implant can be prevented.

Moreover, after an operation of planting of an implant, prognostic defects such as loosening of a screw inside the implant, breakage of the implant and the like can be prevented.

DESCRIPTION OF EMBODIMENTS

Embodiments of the present invention will be described below in detail using examples by referring to the attached drawings. The present invention is not limited to the following embodiments.

Embodiment 1

Figure 1:
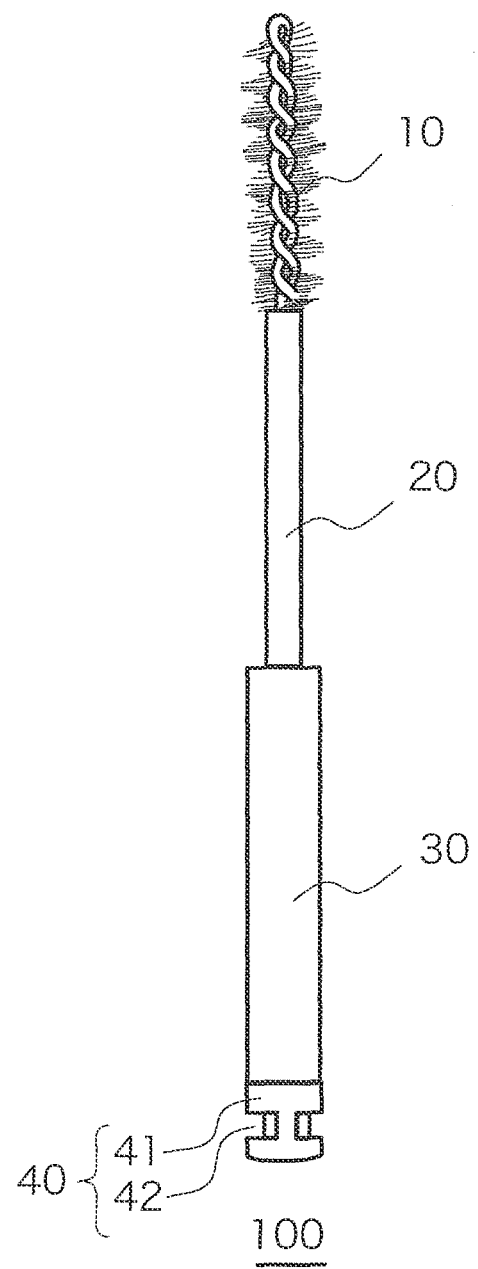
FIG. 1 is a schematic front view illustrating a brush for cleaning the inside of an implant according to the present invention.
Figure 2:
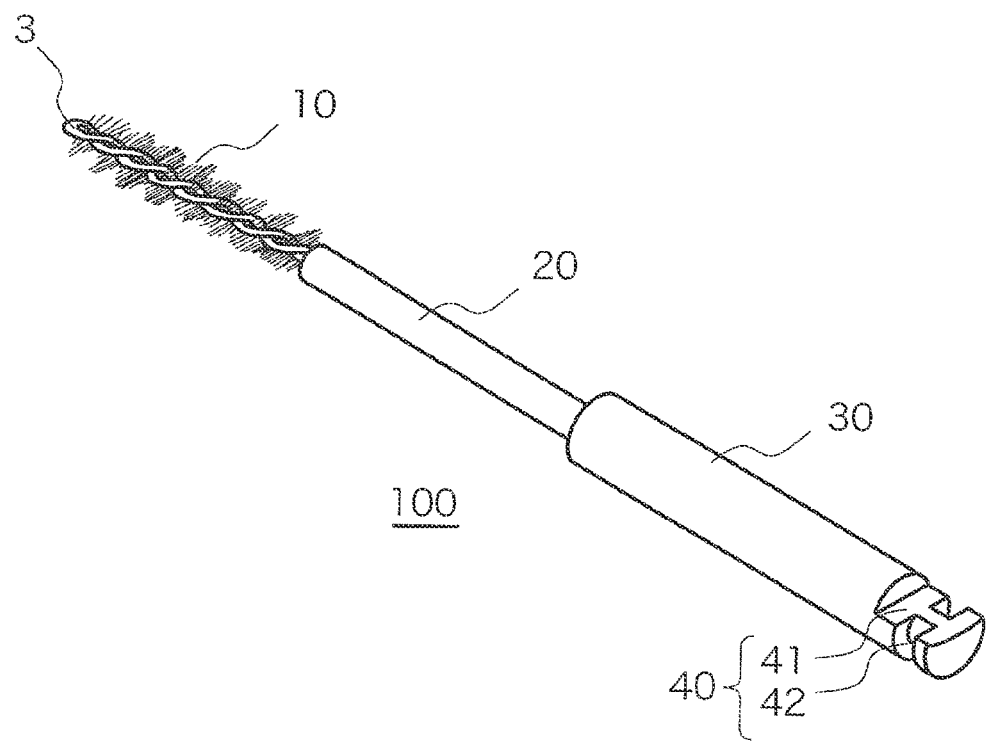
FIG. 2 is a schematic perspective view illustrating a brush for cleaning the inside of an implant according to the present invention.

FIG. 1 is a schematic front view illustrating a brush for cleaning the inside of an implant according to the present invention. Moreover, FIG. 2 is a schematic perspective view illustrating the brush for cleaning the inside of an implant according to the present invention.

The brush 100 for cleaning the inside of an implant according to the present invention is provided with a twisted brush part 10 in which helical brush bristles are formed around a wire rod.

Moreover, the brush 100 for cleaning the inside of an implant according to the present invention is provided with an intermediate columnar part 20 to which the twisted brush part 10 is fixed and a main columnar part 30 to which the intermediate columnar part is fixed.

The main columnar part 30 has a rotating device mounting part 40 on an end portion on the side opposite to an end portion to which the intermediate columnar part 20 is fixed. By fitting and fixing this rotating device mounting part 40 in a rotating device (not shown), the brush 100 for cleaning the inside of an implant can be rotated and used.

FIGS. 2 to 5 are schematic diagrams for explaining steps of forming the twisted brush part 10 in which the helical brush bristles are formed around the wire rod.

Figure 3:
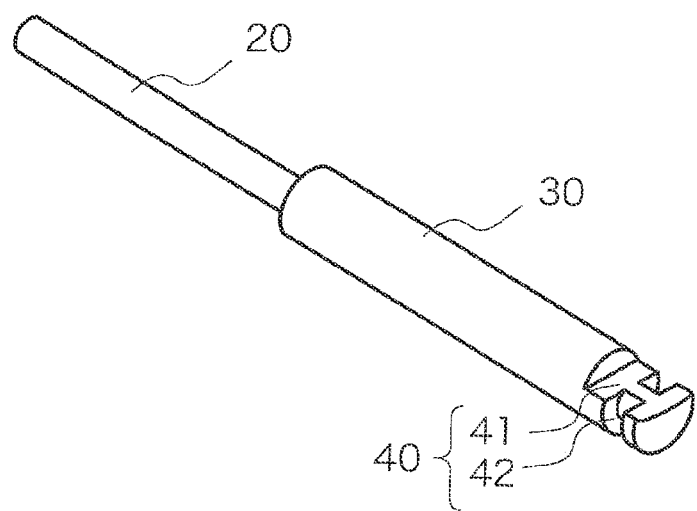
FIG. 3 is a schematic diagram for explaining a step of forming a twisted brush part in which helical brush bristles are formed around a wire rod.

The intermediate columnar part 20 and the main columnar part 30 illustrated in FIG. 3 are formed of metal such as stainless, titanium and the like. Instead of the material of metal or the like or together with the material of metal or the like, inorganic materials such as ceramics and the like and organic materials such as super engineered plastic and the like can be also used.

The intermediate columnar part 20 and the main columnar part 30 illustrated in FIG. 3 can be formed by cutting a metal rod while rotating the same or the like. Moreover, the rotating device mounting part 40 of the main columnar part 30 can be also obtained by cutting the main columnar part 30 while rotating the same or the like and cutting the same using a cutting and polishing device such as a grinder or the like.

Alternatively, the similar shape can be also formed by forming a mold in advance and pouring molten metal or the like into the mold and cooling and then removing the mold.

Figure 4:
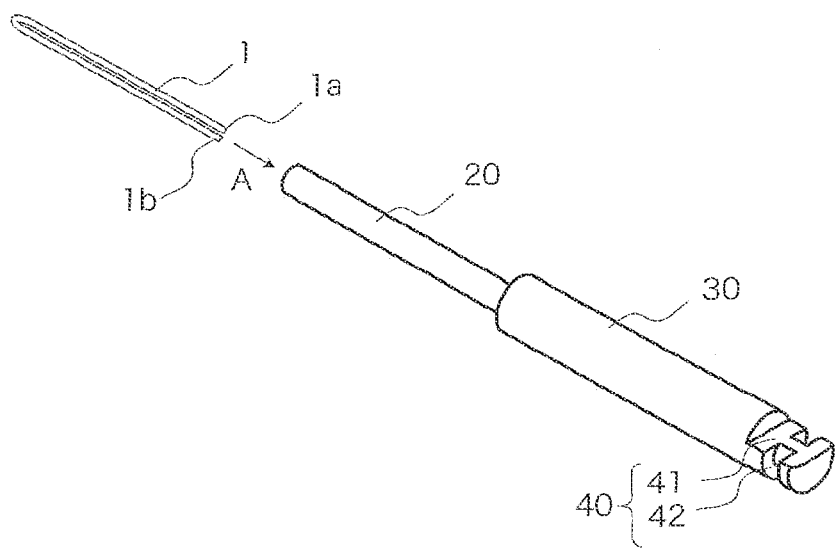
FIG. 4 is a schematic diagram for explaining a step of forming the twisted brush part in which the helical brush bristles are formed around the wire rod.

Subsequently, as illustrated in FIG. 4, both end portions 1a and 1b obtained by smoothly bending a single wire rod 1 at the center part and folding it back are fixed to one end of the intermediate columnar part 20. The wire rod 1 is formed of metal such as stainless and the like.

Moreover, as a method of fixing the both end portions 1a and 1b of the wire rod 1 to the one end of the intermediate columnar part 20, a method of welding or the like, for example, can be cited. Specifically, a method of applying a high voltage to each of the both end portions 1a and 1b of the wire rod and the intermediate columnar part 20 and by connecting the both by bringing them into contact with each other and melting them or the like can be used.

When the both end portions 1a and 1b of the wire rod are to be fixed to the intermediate columnar part 20, it is possible to provide an insertion hole in one end of the intermediate columnar part 20 in advance so that the both end portions 1a and 1b of the wire rod are inserted into this insertion hole and connected by welding or the like.

Figure 5:
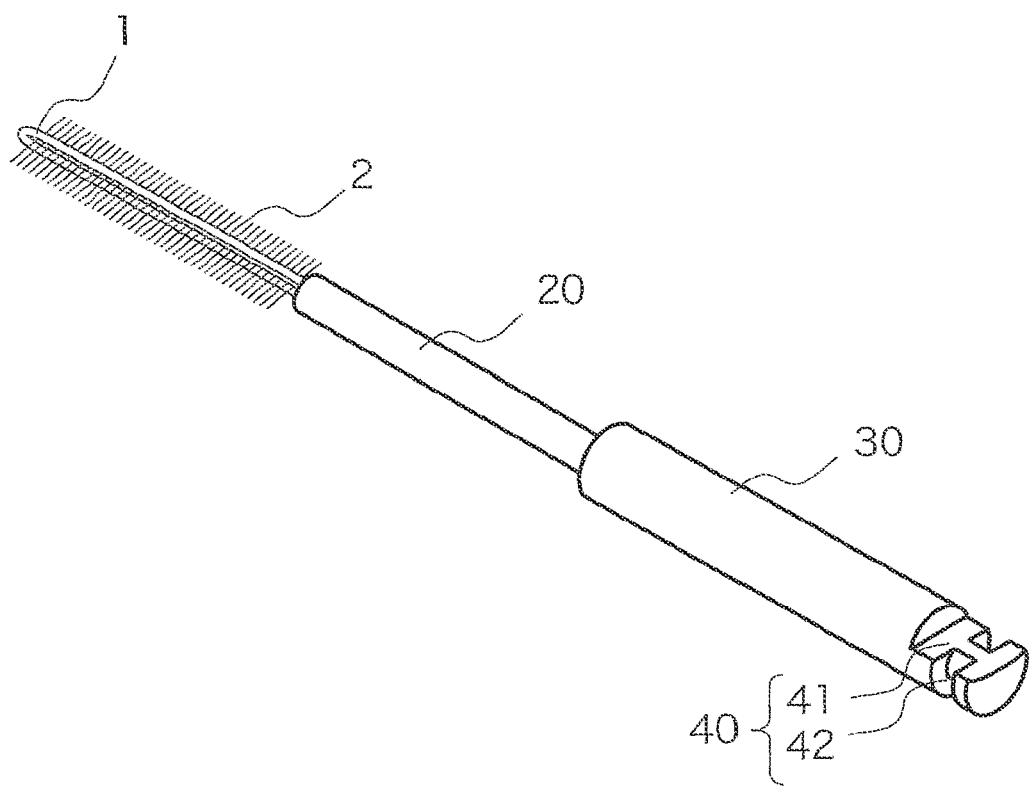
FIG. 5 is a schematic diagram for explaining a step of forming the twisted brush part in which the helical brush bristles are formed around the wire rod.

Subsequently, as illustrated in FIG. 5, a large number of resin fibers 2 are arranged in parallel on the two wire rod parallel parts obtained by smoothly bending and folding back the single wire rod 1 at the center part.

The resin fibers 2 used in the present invention are not particularly limited but synthetic fibers with flexibility such as polyethylene, polypropylene, polyester and the like can be cited, for example.

Subsequently, as illustrated in FIG. 2, by twisting the two wire rod parallel parts obtained by smoothly bending and folding back the single wire rod 1 at the center part, a distal end portion 3 of the twisted brush part 10 can be formed having a smooth curved shape, and helical brush bristles can be formed around the wire rod.

The distal end portion 3 of the twisted brush part 10 used in the present invention has a smooth curved shape and has no portion folded back at a sharp angle and thus, an accident that a stress is applied to a sharp angle portion of the twisted brush part 10 when the twisted brush part 10 is rotated and the wire rod 1 is fractured and the like can be prevented.

Moreover, even if the distal end portion 3 of the rotating twisted brush part 10 touches the gingiva in an oral cavity or the like by mistake, since the distal end portion 3 of the twisted brush part 10 has a smooth curved shape, the gingiva in the oral cavity or the like is not injured.

If the gingiva in the oral cavity or the like is injured, it bleeds, but since this bleeding can be prevented, contamination inside the implant caused by bleeding or the like can be prevented.

The case in which the single wire rod 1 is used is explained in FIGS. 2 to 5, but in the present invention, two or more wire rods 1 can be also used.

Figure 6:
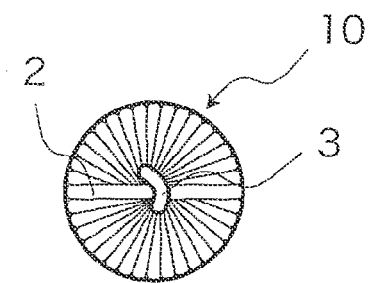
FIG. 6 is a schematic front view illustrating a state in which the brush for cleaning the inside of an implant according to the present invention is observed from the same direction as an arrow A in FIG. 4.

FIG. 6 is a schematic front view illustrating a state in which the brush 100 for cleaning the inside of an implant according to the present invention is observed from the same direction as a direction of an arrow A in FIG. 4.

In FIG. 6, only the twisted brush part 10 is observed, and the intermediate columnar part 20 cannot be observed.

This is because a projection plate of the intermediate columnar part 20 from a major axis center line direction to a plane perpendicular to the major axis center line (the arrow A direction in FIG. 4) of the intermediate columnar part 20 is contained within a projection plane of the twisted brush part 10 from the major axis center line to a plane perpendicular to the major axis center line of the intermediate columnar part 20.

As described above, since a sectional area by the plane perpendicular to the major axis center line of the intermediate columnar part 20 has a size equal to or smaller than a sectional area of the twisted brush part 10 by the plane perpendicular to the major axis center line of the intermediate columnar part 20, when the twisted brush part 10 is inserted into the internal cavity provided in the fixture constituting the implant while being rotated, the rotating intermediate columnar part 20 does not touch the gingival part in the vicinity of the fixture, and the gingival part in the vicinity of the fixture is not injured while the internal cavity provided in the fixture constituting the implant is being cleaned.

Moreover, a length in the major axis direction of the intermediate columnar part 20 used in the present invention is, assuming the length in the major axis direction of the twisted brush part 10 is 1, within a range of 0.8 to 2.0. That is, the brush 100 for cleaning the inside of an implant according to the present invention is provided with the intermediate columnar part 20 having a length long enough to clean the internal cavity provided in the fixture constituting the implant as compared with the twisted brush part 10.

Thus, when the internal cavity provided in the fixture constituting the implant is cleaned, the main columnar part 30 of the rotating brush 100 for cleaning the inside of an implant does not touch the gingival part in the vicinity of the fixture, and the gingival part in the vicinity of the fixture is not injured during cleaning of the internal cavity provided in the fixture constituting the implant.

Moreover, in the present invention, the projection plane of the intermediate columnar part 20 from the major axis center line direction to the plane perpendicular to the major axis center line of the intermediate columnar part 20 is contained within the projection plane of the main columnar part 30 from the major axis center line direction to the plane perpendicular to the major axis center line of the main columnar part 30.

Thus, since the maximum sectional area by the plane perpendicular to the major axis center line of the main columnar part 30 is equal to or larger than the sectional area by the plane perpendicular to the major axis center line direction of the intermediate columnar part 20, the brush 100 for cleaning the inside of an implant according to the present invention can maintain sufficient strength as a whole. Moreover, sufficient fixing strength can be also exerted when the brush 100 for cleaning the inside of an implant according to the present invention is mounted on the rotating device.

In addition, because of presence of the intermediate columnar part 20, visibility does not get worse since the twisted brush part 10 is covered by the main columnar part 30 but the twisted brush part 10 can be easily observed from outside, workability during cleaning of the inside of an implant is excellent.

Each of the intermediate columnar part 20 and the main columnar part 30 used in the present invention may have a polygonal columnar shape but in view of prevention of an injury when the rotated brush 100 for cleaning the inside of an implant according to the present invention touches other teeth, the gingiva and the like in the oral cavity, the shape is preferably columnar.

The major axis center line of the intermediate columnar part in the present invention means the center of gravity line in the major axis direction of the intermediate columnar part, and the major axis center line of the main columnar part means the center of gravity line in the major axis direction in the main columnar part except the rotating device mounting part.

The reason why the rotating device mounting part 40 is excluded from the main columnar part 30 is that since the rotating device mounting part 40 has a portion partially cut off by a plane in parallel with the major axis direction of the main columnar part 30, the position of the center of gravity line is different between the portion with the rotating device mounting part 40 in the main columnar part 30 and the portion without the rotating device mounting part 40.

Moreover, in order to prevent vibration when the brush 100 for cleaning the inside of an implant according to the present invention is rotated, the center of gravely line in the major axis direction of the twisted brush part 10, the center of gravity line in the major axis direction of the intermediate columnar part 20, and the center of gravity line in the major axis direction except the rotating device mounting part 40 in the main columnar part 30 preferably match each other.

Subsequently, the size of the brush 100 for cleaning the inside of an implant according to the present invention will be described.

On the basis of the sectional plane in the direction perpendicular to the major axis center line direction of the intermediate columnar part 20, assuming that the maximum diameter of the main columnar part 30 is 1, the maximum diameter of the twisted brush part 10 is preferably within a range of 0.7 to 1.5, more preferably within a range of 0.8 to 1.3 or still more preferably within a range of 0.9 to 1.1.

Similarly, on the basis of the sectional plane in the direction perpendicular to the major axis center line direction of the intermediate columnar part 20, assuming that the maximum diameter of the main columnar part 30 is 1, the maximum diameter of the intermediate columnar part 20 is preferably within a range of 0.9 to 0.1, more preferably within a range of 0.8 to 0.2 or still more preferably within a range of 0.7 to 0.4.

The length of the intermediate columnar part 20 is, as described above, within a range of 0.8 to 2.0, assuming that the length of the twisted brush part 10 is 1.

Here, the length of the twisted brush part 10 means the length from one end of the intermediate columnar part 20 on the side where the twisted brush part 10 is installed to the distal end of the twisted brush part 10 on the basis of the major axis center line of the intermediate columnar part 20. The same applies to the following.

Regarding the brush 100 for cleaning the inside of an implant according to the present invention, it is preferable that the length in the major axis direction of the twisted brush part 10 is 8 mm±3 mm, the length in the major axis direction of the intermediate columnar part 20 is 9 mm±3 mm, and the length in the major axis direction of the main columnar part 30 is 17 mm±5 mm.

Moreover, it was found out by the examination of the inventor that workability is the best if the maximum diameter of the intermediate columnar part 20 appearing on a section in the direction perpendicular to the major axis center line direction of the intermediate columnar part 20 is 1 mm±0.3 mm, and a maximum diameter of the main columnar part 30 appearing on a section in the direction perpendicular to the major axis center line direction of the main columnar part 30 is 2.1 mm±1 mm.

In the present invention, at least one selected from a group consisting of the wire rod 1 of the twisted brush part 10, the intermediate columnar part 20, and the main columnar part 30 is preferably covered by a resin.

The resin used for the covering can be a polyolefin resin such as polyethylene, polypropylene and the like, a polyester resin such as polyethylene terephthalate, polybutylene terephthalate and the like, poyfluoride resin such as polytetrafluoroethylene and the like, for example.

It is needless to say that the shape or the size of the brush 100 for cleaning the inside of an implant according to the present invention can be changed as appropriate and selected in accordance with the shape or size of the implant to be actually used.

Embodiment 2

Subsequently, a method of cleaning the inside of an implant using the brush 100 for cleaning the inside of an implant according to the present invention will be described.

Figure 7:
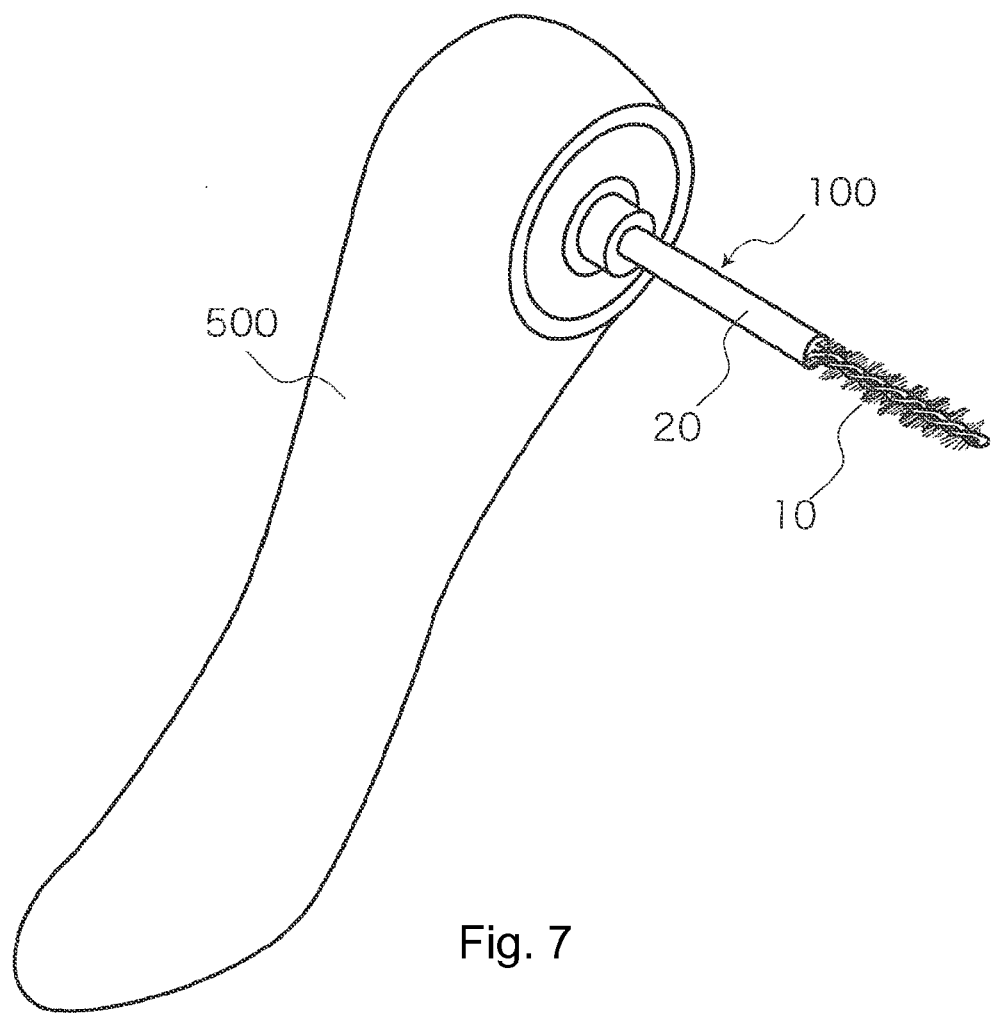
FIG. 7 is a schematic perspective view for explaining a state in which the brush for cleaning the inside of an implant obtained by Embodiment 1 is attached to a rotating device.
Figure 8:
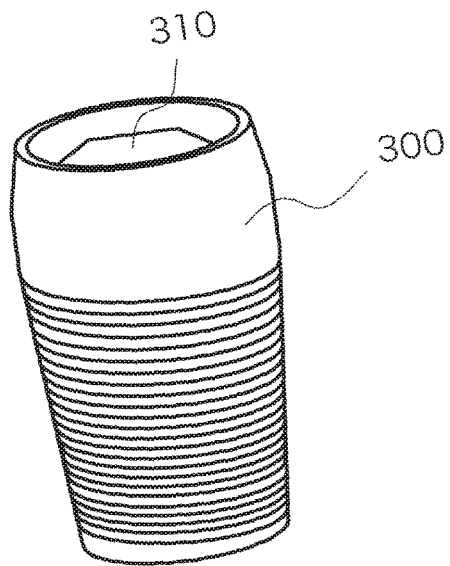
FIG. 8 is a schematic perspective view of a fixture used in a prior-art implant.

FIG. 7 is a schematic perspective view for explaining a state in which the brush 100 for cleaning the inside of an implant obtained by Embodiment 1 is attached to a rotating device 500.

As illustrated above in FIG. 1, the brush 100 for cleaning the inside of an implant according to the present invention has the rotating device mounting part 40 on the main columnar part 30.

The rotating device mounting part 40 includes a notched part 41 provided in a planar direction horizontal to the major axis direction of the main columnar part 20 and a groove part 42 provided in an outer periphery of the main columnar part.

As illustrated in FIG. 7, by mounting the rotating device mounting part 40 on the rotating device 500, the brush 100 for cleaning the inside of an implant can be fixed to the rotating device 500.

Subsequently, the twisted brush part 10 of the brush 100 for cleaning the inside of an implant is inserted by the rotating device 500 into the inside of the implant, that is, the internal cavity provided in the fixture constituting the implant while being rotated.

A rotation speed of the brush 100 for cleaning the inside of an implant is preferably within a range of 100 to 1000 rpm, more preferably within a range of 200 to 900 rpm or further preferably within a range of 400 to 800 rpm.

If the rotation speed of the brush 100 for cleaning the inside of an implant is less than 100 rpm, cleaning efficiency of the inside of the implant is low, while if the speed exceeds 1000 rpm, there is a concern that the brush injures the gingiva in the vicinity of the fixture constituting the implant.

A rotation direction of the brush 100 for cleaning the inside of an implant is determined by a helical shape of the twisted brush 10.

The twisted brush 10 used in the present invention has a helical shape.

In FIG. 6, when the twisted brush 10 is seen from the front, if the helical shape if formed leftwise, by rotating the twisted brush 10 in the left direction when seen from the front, adhering objects such as a bone fragment, a gingival fragment, blood or the like of the patient adhering to the helical brush of the twisted brush 10 or food residues generated during daily meals and the like are discharged to the side opposite to the distal end of the twisted brush 10, that is, to the intermediate columnar part 20 side.

Actually, after checking whether the helical shape of the twisted brush 10 is formed leftwise or rightwise by using a magnifying glass or the like and adjusting the rotation direction to a direction in which the adhering objects such as food residues inside the implant are discharged to the outside when the twisted brush 10 of the brush 100 for cleaning the inside of an implant is inserted into the inside of the implant, that is, the internal cavity of the fixture while being rotated, actual cleaning is carried out.

As described above, cleaning of the inside of an implant can be carried out simply and safely by using the brush 100 for cleaning the inside of an implant.

Embodiment 3

A brush 200 for cleaning the inside of an implant according to an embodiment 3 is a variation of the brush 100 for cleaning the inside of an implant according to Embodiment 1.

In the brush 100 for cleaning the inside of an implant according to Embodiment 1, brush bristles are not installed on the distal end portion 3 of the twisted brush part 10 in the major axis center line direction of the intermediate columnar part 20. On the other hand, the brush 200 for cleaning the inside of an implant according to Embodiment 3 is different in a point that brush bristles are installed on the distal end portion of the twisted brush part in the major axis center line direction of the intermediate columnar part 20. Other than this point, the brush 200 for cleaning the inside of an implant according to Embodiment 3 is similar to the case of the brush 100 for cleaning the inside of an implant according to Embodiment 1.

FIGS. 9 to 13 are schematic diagrams for explaining a step of forming the twisted brush part 10 in which helical brush bristles are formed on the distal end portion of the twisted brush part.

Figure 9:
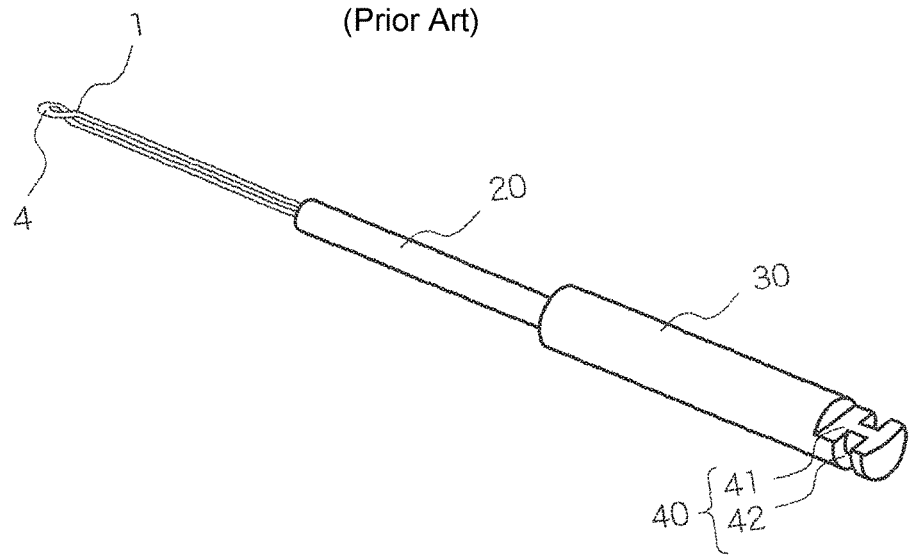
FIG. 9 is a schematic diagram for explaining a step of forming the twisted brush part in which the helical brush bristles are formed at a distal end portion of the twisted brush part.

As illustrated in FIG. 9, an annular part 4 is formed at a distal end of the twisted brush part by twisting the wire rod 1 of the twisted brush part.

Figure 10:
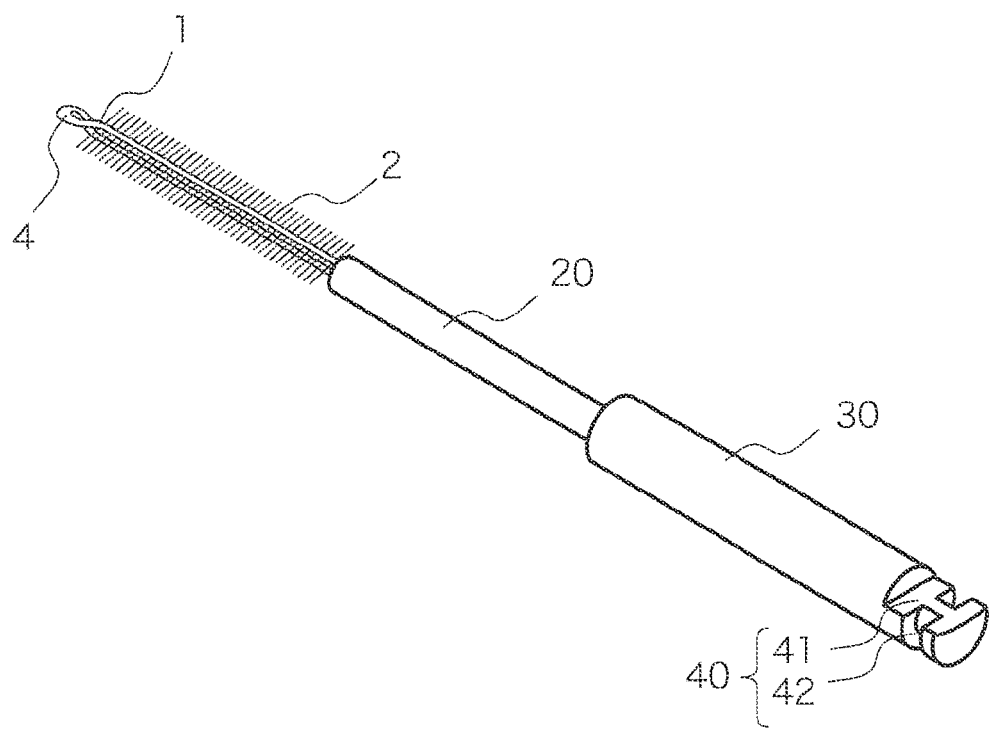
FIG. 10 is a schematic diagram for explaining a step of forming the twisted brush part in which the helical brush bristles are formed at the distal end portion of the twisted brush part.

Subsequently, as illustrated in FIG. 10, similarly to the step illustrated in FIG. 5 in the case of the above-described embodiment 1, a large number of the resin fibers 2 are arranged in parallel with the two wire rod parallel parts formed of the single wire rod 1.

Figure 11:
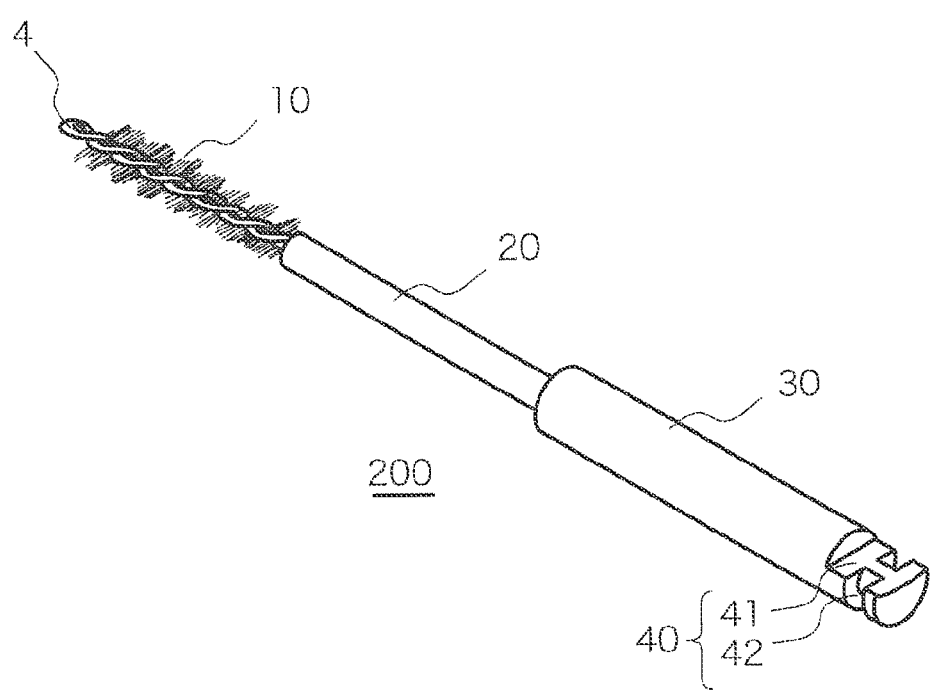
FIG. 11 is a schematic diagram for explaining a step of forming the twisted brush part in which the helical brush bristles are formed at the distal end portion of the twisted brush part.

Subsequently, as illustrated in FIG. 11, by twisting the two wire rod parallel parts obtained by folding back the single wire rod 1, the helical brush bristles can be formed around the wire rod 1.

Figure 12:
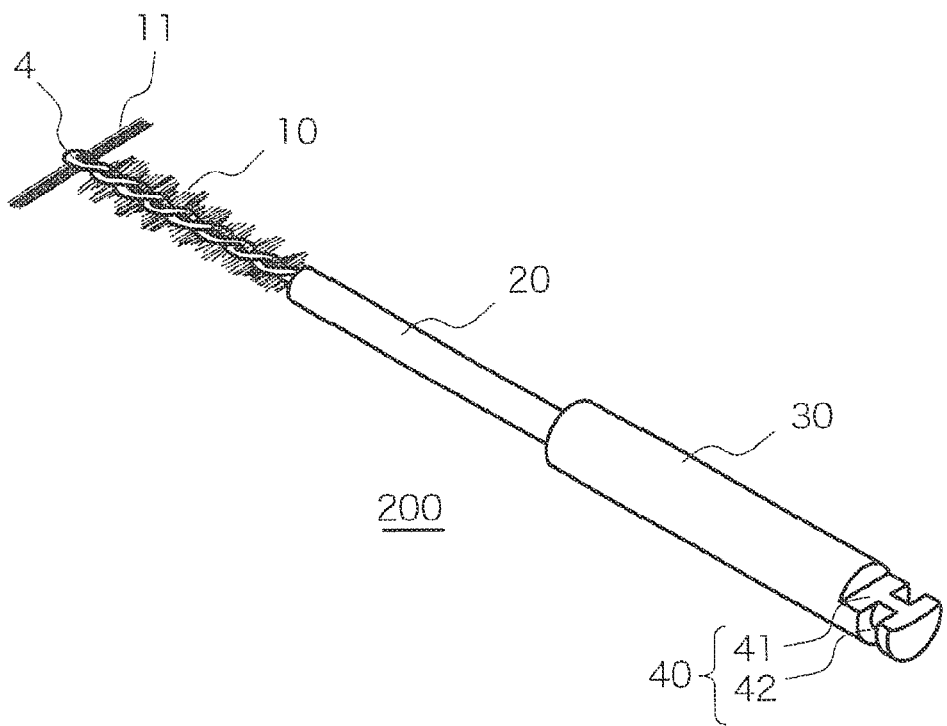
FIG. 12 is a schematic diagram for explaining a step of forming the twisted brush part in which the helical brush bristles are formed at the distal end portion of the twisted brush part.

Subsequently, as illustrated in FIG. 12, a large number of resin fibers 11 are passed through the annular part 4 at the distal end of the twisted brush part. The large number of resin fibers 11 are folded in the major axis center line direction of the intermediate columnar part 20.

Figure 13:
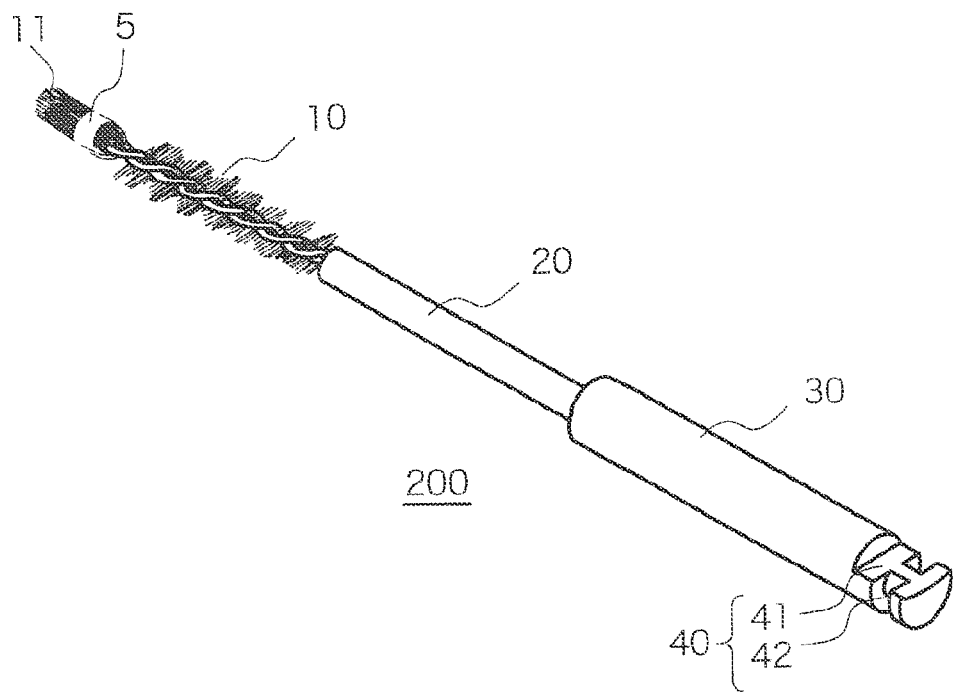
FIG. 13 is a schematic diagram for explaining a step of forming the twisted brush part in which the helical brush bristles are formed at the distal end portion of the twisted brush part.

Brush bristles can be formed on the distal end portion of the twisted brush part illustrated in FIG. 13 by a method of bundling the peripheries of the large number of folded resin fibers 11 with a resin fiber, a method of fixing the periphery of the large number of folded resin fibers 11 with a resin tape and the like.

In FIG. 13, the resin fibers 11 are bundled by the resin fiber 5.

Since the brush 200 for cleaning the inside of an implant according to Embodiment 2 has a large number of resin fibers 11 which are brush bristles on the distal end portion of the twisted brush part, brush bristles can be installed on the distal end portion of the twisted brush part in the major axis center line direction of the intermediate columnar part. By means of these brush bristles, the internal cavity provided in the fixture constituting the implant can be cleaned.

INDUSTRIAL APPLICABILITY

It has been difficult to clean the internal cavity provided in the fixture constituting an implant but by using the brush for cleaning the inside of an implant according to the present invention, the internal cavity provided in the fixture constituting an implant can be easily cleaned.

REFERENCE SIGNS LIST 1 wire rod
1a, 1b both end portions of wire rod
2, 5, 11 resin fiber
3 distal end portion of twisted brush part
4 annular part
10 twisted brush part
20 intermediate columnar part
30 main columnar part
40 rotating device mounting part
41 notched part
42 groove part
100, 200 brush for cleaning the inside of an implant
300 fixture
310 internal cavity provided in fixture constituting implant
500 rotating device
A major axis center line direction

The invention claimed is:

1. A brush for cleaning the inside of an implant comprising:
a twisted brush part comprising a large number of resin fibers and a wire rod, the twisted brush part being formed by arranging the resin fibers in parallel in a direction perpendicular to the wire rod and then twisting said wire rod so as to provide helical brush bristles around said wire rod;
an intermediate columnar part; and
a main columnar part; wherein
the wire rod used in said twisted brush part is fixed to one end portion of said intermediate columnar part so that said twisted brush part and said intermediate columnar part are fixed to each other;
said main columnar part is fixed at a first end portion to an opposite end portion of said intermediate columnar part;
said main columnar part has a rotating device mounting part on a second end portion that is arranged opposite to the first end portion;
a major axis center line of said intermediate columnar part matches a major axis center line of said main columnar part;
wherein along a direction of the major axis center line of said intermediate columnar part, assuming that the length of said twisted brush part is 1, the length of said intermediate columnar part is in a range of 0.8 to 2.0.

2. The brush for cleaning the inside of an implant according to claim 1, wherein
a projection plane of said intermediate columnar part from the major axis center line direction to a plane perpendicular to the major axis center line of said intermediate columnar part is contained within a projection plane of said twisted brush part from the major axis center line direction to the plane perpendicular to the major axis center line of said intermediate columnar part; and the projection plane of said intermediate columnar part from the major axis center line direction to the plane perpendicular to the major axis center line of said intermediate columnar part is contained within the projection plane of said main columnar part from the major axis center line direction to the plane perpendicular to the major axis center line direction of said main columnar part.

3. The brush for cleaning the inside of an implant according to claim 2, wherein
said twisted brush part is formed by arranging the large number of resin fibers in parallel with two wire rod parallel parts obtained by smoothly bending and folding back one wire rod and then, by twisting said two wire rod parallel parts so as to form a distal end portion of said twisted brush part having a smooth curved shape and by forming helical brush bristles around said wire rod.

4. The brush for cleaning the inside of an implant according to claim 3, wherein
the rotating device mounting part of said main columnar part includes a notched part provided in a planar direction horizontal to the major axis direction of said main columnar part and a groove part provided in an outer periphery of said main columnar part.

5. The brush for cleaning the inside of an implant according to claim 4, wherein
the distal end portion of said twisted brush part is provided with longitudinal brush bristles in the major axis center line direction of said intermediate columnar part.

6. The brush for cleaning the inside of an implant according to claim 5, wherein
at least one selected from a group consisting of the wire rod of said twisted brush part, the intermediate columnar part, and said main columnar part is covered by a resin.

7. The brush for cleaning the inside of an implant according to claim 6, wherein
a length in the major axis direction of said twisted brush part is 8 mm±3 mm, a length in the major axis direction of said intermediate columnar part is 9 mm±3 mm, and a length in the major axis direction of the said main columnar part is 17 mm±5 mm; and
a maximum diameter appearing on a section in the direction perpendicular to the major axis direction of said intermediate columnar part is 1 mm±0.3 mm, and a maximum diameter appearing on a section in the direction perpendicular to the major axis direction of said main columnar part is 2.1 mm±1 mm.

* * * * *